United States Patent
Chiang

(10) Patent No.: US 9,907,631 B2
(45) Date of Patent: Mar. 6, 2018

(54) QUICK CONNECTOR FOR ORAL IRRIGATOR

(71) Applicant: STAMPRO METAL INDUSTRY CO., LTD., Taichung (TW)

(72) Inventor: Shui-Tung Chiang, Taichung (TW)

(73) Assignee: STAMPRO METAL INDUSTRY CO., LTD., Taichung (TW)

( * ) Notice: Subject to any disclaimer, the term of this patent is extended or adjusted under 35 U.S.C. 154(b) by 485 days.

(21) Appl. No.: 14/628,038

(22) Filed: Feb. 20, 2015

(65) Prior Publication Data
US 2016/0184064 A1 Jun. 30, 2016

(30) Foreign Application Priority Data
Dec. 24, 2014 (TW) .............................. 103145295 A

(51) Int. Cl.
*F16L 17/00* (2006.01)
*A61C 17/02* (2006.01)

(52) U.S. Cl.
CPC ................................ *A61C 17/0214* (2013.01)

(58) Field of Classification Search
USPC .......................... 285/360, 376, 401; 601/165
See application file for complete search history.

(56) References Cited

U.S. PATENT DOCUMENTS

| | | | | |
|---|---|---|---|---|
| 1,916,449 A | * | 7/1933 | Tompkins | F16L 19/0218 285/376 |
| 3,227,380 A | * | 1/1966 | Pinkston | A61C 17/0214 601/165 |
| 4,613,162 A | * | 9/1986 | Hughes | E21B 33/038 285/376 |
| 4,688,633 A | * | 8/1987 | Barkley | E21B 33/03 16/341 |
| 4,691,790 A | * | 9/1987 | Reichman | E21B 7/18 285/376 |
| 6,250,688 B1 | * | 6/2001 | Kirby | F16L 49/06 285/360 |

FOREIGN PATENT DOCUMENTS

| | | |
|---|---|---|
| TW | 429779 U | 4/2001 |
| TW | 579834 U | 3/2004 |
| TW | M249923 U | 11/2004 |

* cited by examiner

*Primary Examiner* — Gregory J Binda
(74) *Attorney, Agent, or Firm* — Muncy, Geissler, Olds & Lowe, P.C.

(57) ABSTRACT

A quick connector includes a socket including a threaded portion detachably fastenable to a water tap, an opposing free end portion and three inside flanges equiangularly spaced between the threaded portion and the free end portion, and a connection member including a connector body defining an axial through hole in communication with the socket and a fitting defining three insertion grooves for the insertion of the respective inside flanges and three sliding grooves respectively connected to the insertion grooves corresponding to the three inside flanges and disposed adjacent to the position-limit surface for allowing sliding therein of the respective inside flanges. Thus, the user can use to the quick connector to rapidly and detachably connect an oral irrigator to a water tap in a convenient and hygienic manner, avoiding the problem that oral irrigator cannot effectively clean tartar due to insufficient water pressure caused by a leakage of water.

7 Claims, 5 Drawing Sheets

QUICK CONNECTOR FOR ORAL IRRIGATOR

BACKGROUND OF THE INVENTION

1. Field of the Invention

The present invention relates to connector technology and more particularly, to a quick connector adapted for rapidly and detachably connecting an oral irrigator to a water tap.

2. Description of the Related Art

Food debris left in the mouth and the teeth can easily lead to tooth decay and gum disease, so cleaning residual food from the mouth is an important measure for the prevention of oral diseases. Many oral hygiene aids are known, such as toothbrushes, dental floss, oral irrigator etc.

Various oral irrigators are seen in prior art patents. Exemplars are seen in Taiwan Patent 429779, entitled "Improved structure of oral irrigator"; Taiwan Patent 579834, entitled "Improved structure of oral irrigator"; Taiwan Patent M249623, entitled "Improved structure of oral irrigator". These prior art oral irrigators commonly comprise a handle of a one-piece design of tubular member, a water inlet located at one end of the handle, a jet nozzle located at an opposite end of the handle, and a water channel connected between the water inlet and the jet nozzle. Clean water from an external water source or cleaning solution is guided into the water inlet and forced through the water channel out of the jet nozzle and ejected onto the user's gum in an orthogonal manner to clean the gum.

For ease of use, a changeover connector may be provided between the water tap and the oral irrigator. As illustrated in FIG. 1, the water inlet of the oral irrigator 1 has a flexible water hose 2 connected thereto. The opposite end of the flexible water hose 2 is connected to the changeover connector 3. The changeover connector 3 is thread-connected to the water tap 4 and the water outlet 5. Thus, the user can selectively switch the changeover connector 3 to let water flow out of the changeover connector 3 through a bottom end of the changeover connector 3 or into the oral irrigator 1. However, after a long use, the pivoting part of the changeover connector can be loosened, leading to water leakage. When a water leak problem occurs, the water pressure at the water outlet end of the oral irrigator will become insufficient for cleaning tartar off the teeth. When this problem occurs, the whole changeover connector must be replaced. This manner is inconsistent with the economic benefits. Further, if the changeover connector is provided for use by different users, a user usually will detach the oral irrigator from the changeover connector after cleaned the mouth with the flexible water hose left connected to the changeover connector, facilitating a next user to use the changeover connector. However, it is inconvenient to use the water tap in this manner and not easy to receive the flexible water hose that is left at changeover connector. Therefore, this prior art changeover connector is not an ideal design.

SUMMARY OF THE INVENTION

The present invention has been accomplished under the circumstances in view. It is the main object of the present invention to provide a quick connector for oral irrigator, which can be used to rapidly and detachably connect an oral irrigator to a water tap in a convenient and hygienic manner, avoiding the problem that oral irrigator cannot effectively clean tartar due to insufficient water pressure caused by a leakage of water.

To achieve this and other objects of the present invention, a quick connector for oral irrigator comprises a socket and a connection member. The socket is a hollow tube, comprising a threaded portion axially located at one end thereof and threadable into a water outlet of a water tap, a free end portion axially located at an opposite end thereof, and three inside flanges equiangularly located at an inside wall thereof between the threaded portion and the free end portion. The connection member comprises a connector body and a fitting connected to the connector body. The connector body comprises an axial through hole disposed in communication with the socket. The fitting comprises an outer wall, an inner wall, a position-limit surface located at a bottom side of the inner wall, and three insertion grooves and three sliding grooves respectively disposed corresponding to the inside flanges. The sliding grooves are respectively connected to the insertion grooves adjacent to the position-limit surface, and adapted for the insertion of the inside flanges for enabling the inside flanges to be slidably coupled to the sliding grooves.

Preferably, the fitting of the connector body further comprises three stop surfaces respective located between each two adjacent sliding grooves.

Preferably, the quick connector further comprises a water filter mounted in the socket adjacent to the water outlet of the water tap. Further, the water filter comprises a plurality of filter holes.

Preferably, the socket further comprises a positioning portion extending around and inwardly curved in the inside wall thereof. Further, the water filter comprises an extension portion extending around the periphery thereof and stopped at the positioning portion of the socket.

Preferably, the quick connector further comprises a first seal ring mounted between the water filter and the water outlet of the water tap.

Preferably, the socket comprises a driving bevel surface located at each inside flange adjacent to the associating insertion groove and the associating sliding groove. Further, the connection member comprises a plurality of engagement ribs respectively disposed between the respective insertion grooves and the respective associating sliding grooves and projecting from the inner wall toward the outer wall of the fitting. Each engagement rib comprises a driven bevel surface disposed between the associating insertion groove and the associating sliding groove and adapted for respectively mating with one respective driving bevel surface to guide one respective inside flange into one respective sliding groove.

Preferably, the connector body of the connection member comprises a base portion, an adapter column upwardly extended from the base portion, and a connection port downwardly extended from the base portion. Further, the fitting is mounted on the adapter column. Further, the axial through hole of the connector body is disposed in communication between the adapter column and the connection port.

Preferably, the connector body of the connection member further comprises a plurality of ribs extending around the periphery of the base portion.

Preferably, the quick connector further comprises at least one second seal ring. Further, the adapter column comprises at least one locating groove extending around the periphery thereof and respectively adapted for the mounting of the at least one second seal ring.

Preferably, the number of the at least one second seal ring and the number of the at least one locating groove are respectively 2. Further, the locating grooves are spaced from each other at a predetermined distance. Further, one locating groove is disposed in the junction between the adapter column and the base portion.

Thus, the user can use the quick connector to rapidly and detachably connect the oral irrigator to the water tap. Using the quick connector to connect the oral irrigator to the water tap is not only convenient and hygienic, but also can avoid the problem that oral irrigator cannot effectively clean tartar due to insufficient water pressure caused by a leakage of water.

Other advantages and features of the present invention will be fully understood by reference to the following specification in conjunction with the accompanying drawings, in which like reference signs denote like components of structure.

DETAILED DESCRIPTION OF THE INVENTION

Figure 1:
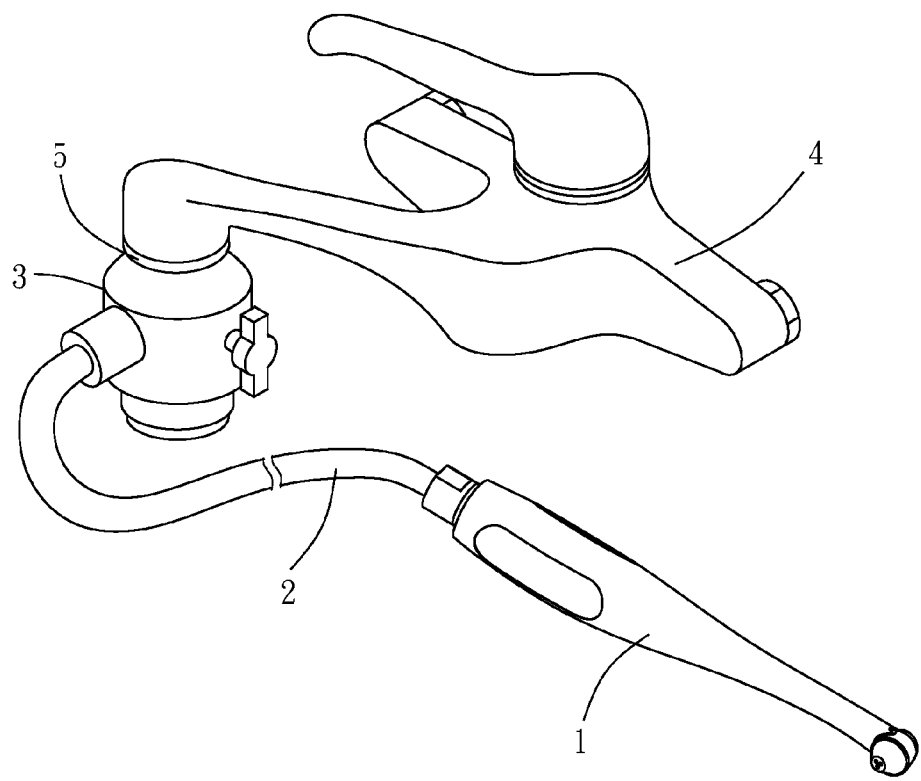
FIG. 1 is an oblique top elevational view illustrating a changeover connector connected between an oral irrigator and a water tap according to the prior art.
Figure 2:
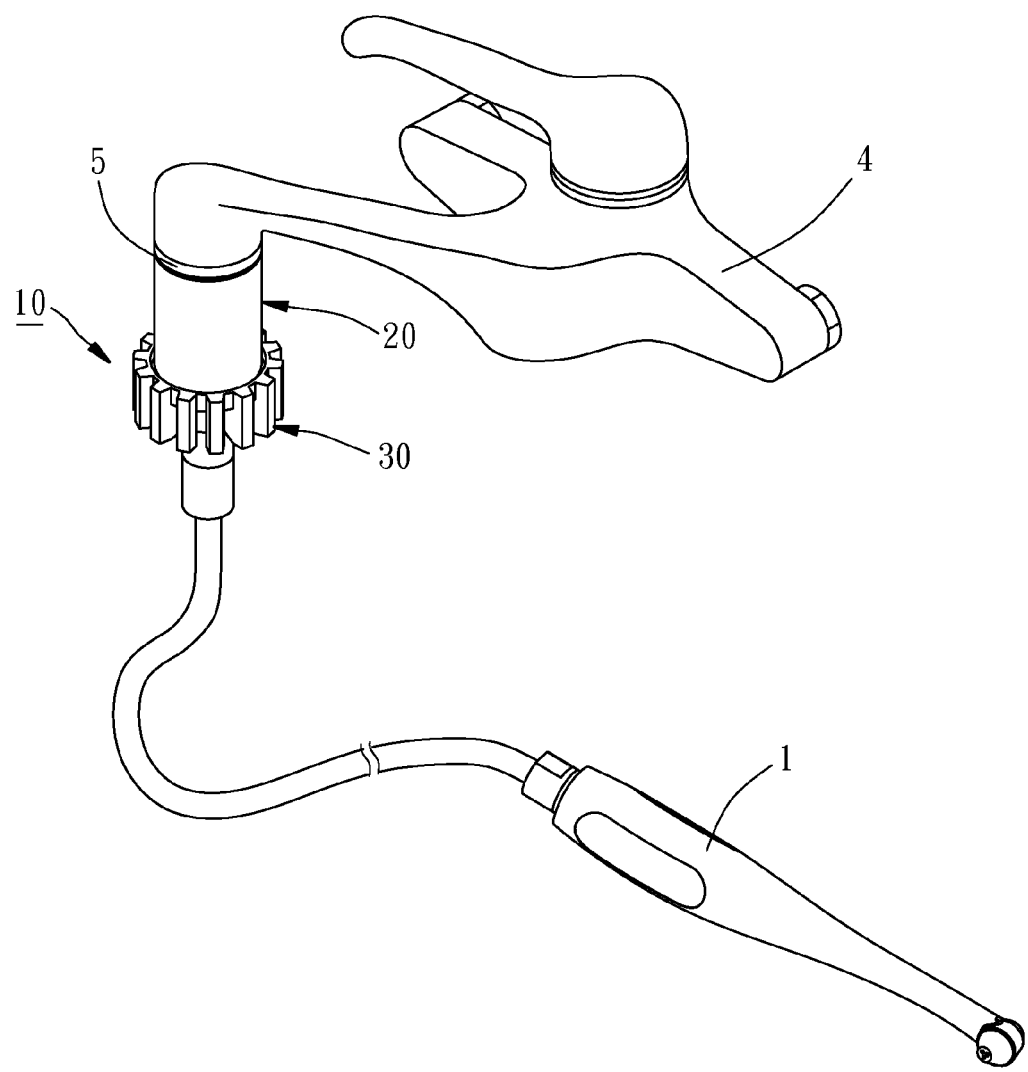
FIG. 2 is an oblique top elevational view illustrating a quick connector connected between an oral irrigator and a water tap in accordance with the present invention.
Figure 3:
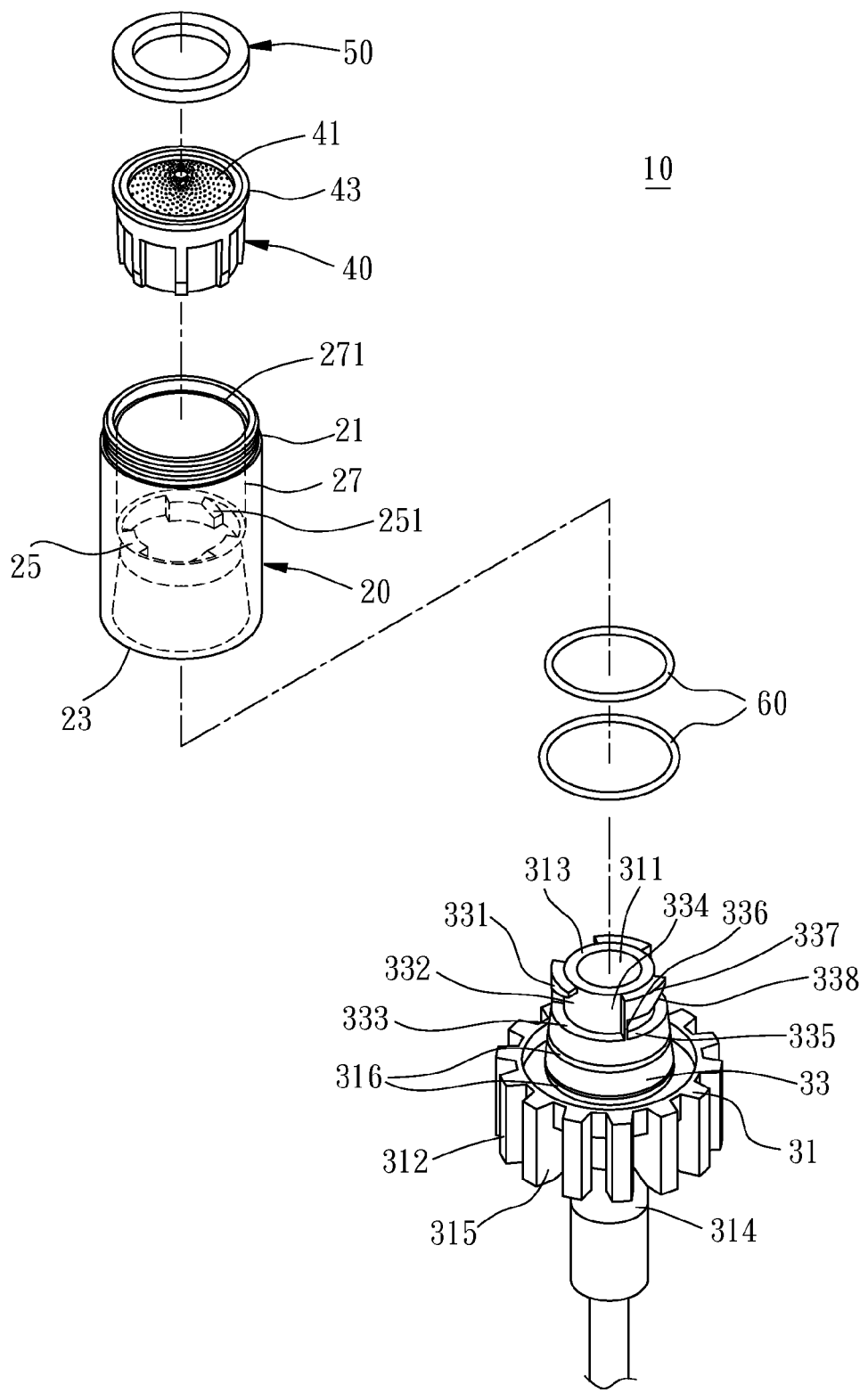
FIG. 3 is an exploded view of the quick connector of the present invention, illustrating the relative positioning and structural details of the component parts of the quick connector.

Referring to FIGS. 2 and 3, a quick connector 10 in accordance with the present invention is adapted for connecting an oral irrigator 1 to a water tap 4. The quick connector 10 comprises a socket 20, a connection member 30, a water filter 40, a first seal ring 50, and at least one second seal ring 60.

The socket 20 is a hollow tube, comprising a threaded portion 21, a free end portion 23 and three inside flanges 25. The threaded portion 21 and the free end portion 23 are respectively axially located at two opposite sides of the socket 20. The threaded portion 21 is threaded into the water outlet 5 of the water tap 4. The three inside flanges 25 are equiangularly located at an inside wall 27 of the socket 20 between the threaded portion 21 and the free end portion 23. The socket 20 further comprises a positioning portion 271 located at the inside wall 27. The positioning portion 271 is inwardly curved in the inside wall 27.

The connection member 30 comprises a connector body 31, and fitting 33 connected to the connector body 31. The connector body 31 comprises a base portion 312, an adapter column 313 upwardly extended from the base portion 312, a connection port 314 downwardly extended from the base portion 312, a plurality of ribs 315 radially spaced around the periphery of the base portion 312 for the holding of the user's hand, at least one locating groove 316 extending around the periphery of the adapter column 313, and an axial through hole 311 axially extending through the adapter column 313, the base portion 312 and the connection port 314. The fitting 33 comprises an outer wall 331, an inner wall 332, a position-limit surface 333 located at a bottom side of the inside flange 25, and three insertion grooves 334, three sliding grooves 335 and three stop surfaces 336 respectively disposed corresponding to the inside flanges 25. The insertion grooves 334 are located in the outer wall 331 to face toward the inner wall 332. The sliding grooves 335 are respectively connected to the insertion grooves 334 and respective abutted to the position-limit surfaces 333. The inside flanges 25 are respectively inserted into the insertion grooves 334 and slidable along the respective sliding grooves 335. The stop surfaces 336 are respectively disposed between each two adjacent sliding grooves 335.

The water filter 40 is mounted in the socket 20 near the water outlet 5 of the water tap 4, comprising a plurality of filter holes 41 for filtering water that flows out of the water outlet 5 of the water tap 4. The water filter 40 further comprises an extension portion 43 for stopping at the positioning portion 271.

The first seal ring 50 is mounted between the water filter 40 and the water outlet 5 of the water tap 4 to enhance the sealing tightness between the positioning portion 271 at the inside wall 27 of the socket 20 and the extension portion 43 of the water filter 40, preventing water leaks and any insufficient water pressure problem of the oral irrigator 1 due to water leakage.

The at least one second seal ring 60 is mounted in the at least one locating groove 316 of the adapter column 313. In this embodiment, the number of the at least one second seal ring 60 and the number of the at least one locating groove 316 of the adapter column 313 are respectively two. Further, the two locating grooves 316 are spaced from each other at a predetermined distance, wherein one locating groove 316 is disposed in the junction between the adapter column 313 and the base portion 312. Thus, multiple protections are provided between the inside wall 27 of the socket 20 and the adapter column 313 of the connection member 30 to enhance the sealing tightness, preventing the problems of water leakage and pressure loss. Further, when the second seal ring 60 that is located at the junction between the adapter column 313 and the base portion 312 touches the free end portion 23 of the socket 20, the second seal ring 60 will feed back a pressure to the socket 20.

Figure 4:
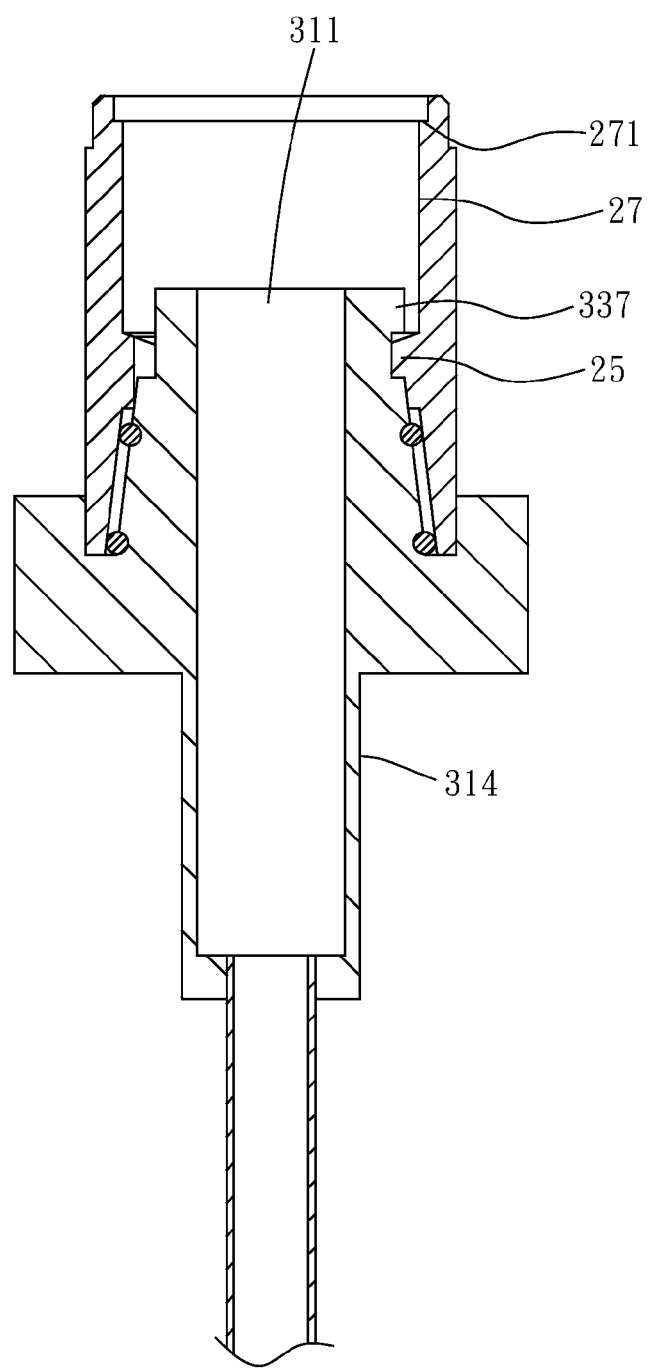
FIG. 4 is a schematic sectional view of the present invention, illustrating the relationship between the socket and the connection member.
Figure 5:
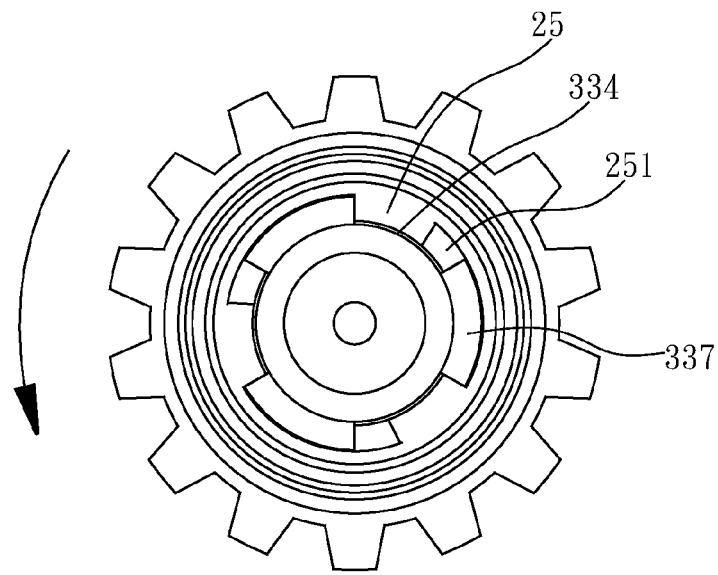
FIG. 5 is a schematic top view of the quick connector of the present invention, illustrating a connection status between the connection member and the socket before locking.
Figure 6:
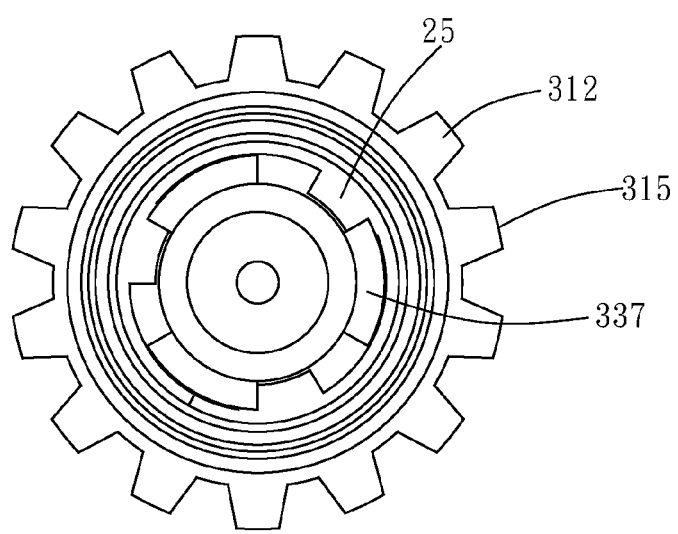
FIG. 6 corresponds to FIG. 5, illustrating the connection member and the socket tightly fastened up.

Further, as shown in FIG. 3 and FIG. 4, the socket 20 further comprises a driving bevel surface 251 located at each inside flange 25 adjacent to the associating insertion groove 334 and the associating sliding groove 335. The connection member 30 further comprises a plurality of engagement ribs 337 respectively disposed between the respective insertion grooves 334 and the respective associating sliding grooves 335. Each engagement rib 337 projects from the inner wall toward the outer wall, comprising a driven bevel surface 338 disposed between the associating insertion groove 334 and the associating sliding groove 335. A mutual guiding action between the driving bevel surfaces 251 and the driven bevel surfaces 338 causes the inside flanges 25 to be respectively moved into the respective sliding grooves 335. Referring also to FIG. 5 and FIG. 6, the procedure of mounting the connection member 30 of the quick connector 10 in the socket 20 is outlined hereinafter. At first insert the inside flanges 25 of the socket 20 into the respective insertion grooves 334 of the connection member 30. At this time, the inside flanges 25 are stopped at the position-limit surface 333 (see FIG. 3). Thereafter, hold the ribs 315 of the connection member 30 with the hand and then rotate the connection member 30 to abut the driving bevel surfaces 251 of the inside flanges 25 against the respective driven bevel surfaces 338 of the engagement ribs 337, causing the inside flanges 25 to be moved along the respective position-limit surfaces 333 into the respective sliding grooves 335 and then respectively stopped at the respective stop surfaces 336. At this time, the second seal ring 60 forces the inside flanges 25 of the socket 20 to abut against the respective engagement ribs 337 of the connection member 30 tightly, achieving the expected packing effect.

Thus, the user can use the quick connector 10 to rapidly and detachably connect the oral irrigator 1 to the water tap 4. Using the quick connector 10 to connect the oral irrigator 1 to the water tap 4 is not only convenient and hygienic, but also can avoid the problem that oral irrigator cannot effectively clean tartar due to insufficient water pressure caused by a leakage of water.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. A quick connector for oral irrigator, comprising:
a socket being a hollow tube, said socket comprising a threaded portion axially located at one end thereof and threadable into a water outlet of a water tap, a free end portion axially located at an opposite end thereof, and three inside flanges equiangularly located at an inside wall thereof between said threaded portion and said free end portion;
a connection member comprising a connector body and a fitting connected to said connector body, wherein said connector body comprises a base portion, an adapter column upwardly extended from said base portion, a connection port downwardly extended from said base portion, and an axial through hole disposed in communication with said socket, said axial through hole is disposed in communication between said adapter column and said connection port; said adapter column comprises two locating grooves extending around the periphery thereof, said locating grooves are spaced from each other at a predetermined distance, one said locating groove being disposed in the junction between said adapter column and said base portion, said fitting is mounted on said adapter column, said fitting comprising an outer wall, an inner wall, a position-limit surface located at a bottom side of said inner wall, and three insertion grooves and three sliding grooves respectively disposed corresponding to said inside flanges, said outer wall is recessed inwardly to form said inner wall, said sliding grooves being respectively connected to said insertion grooves adjacent to said position-limit surface, said insertion grooves being adapted for the insertion of said inside flanges for enabling said inside flanges to be slidably coupled to said sliding grooves; and
two second seal rings, respectively being mounted at said locating grooves.

2. The quick connector for oral irrigator as claimed in claim 1, wherein said fitting of said connector body further comprises three stop surfaces respective located between each two adjacent said sliding grooves.

3. The quick connector for oral irrigator as claimed in claim 1, further comprising a water filter mounted in said socket adjacent to the water outlet of said water tap, said water filter comprising a plurality of filter holes.

4. The quick connector for oral irrigator as claimed in claim 3, wherein said socket further comprises a positioning portion extending around and inwardly curved in the inside wall thereof; said water filter comprises an extension portion extending around the periphery thereof and stopped at said positioning portion of said socket.

5. The quick connector for oral irrigator as claimed in claim 3, further comprising a first seal ring mounted between said water filter and said water outlet of said water tap.

6. The quick connector for oral irrigator as claimed in claim 1, wherein said socket comprises a driving bevel surface located at each said inside flange adjacent to the associating said insertion groove and the associating said sliding groove; said connection member further comprises a plurality of engagement ribs respectively disposed between the respective said insertion grooves and the respective associating said sliding grooves and projecting from said inner wall toward said outer wall of said fitting, each said engagement rib comprising a driven bevel surface disposed between the associating said insertion groove and the associating said sliding groove and adapted for respectively mating with one respective said driving bevel surface to guide one respective said inside flange into one respective said sliding groove.

7. The quick connector for oral irrigator as claimed in claim 1, wherein said connector body of said connection member further comprises a plurality of ribs extending around the periphery of said base portion.

\* \* \* \* \*